United States Patent
Vilenskii (10) Patent No.: US 10,905,331 B2
(45) Date of Patent: Feb. 2, 2021

(54) IMAGE CAPTURING DEVICE AND SENSING PROTECTION DEVICE

(71) Applicant: SAMSUNG ELECTRONICS CO., LTD., Suwon-si (KR)

(72) Inventor: Maxim Alexeevich Vilenskii, Moscow (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 886 days.

(21) Appl. No.: 14/969,992

(22) Filed: Dec. 15, 2015

(65) Prior Publication Data

US 2016/0166150 A1    Jun. 16, 2016

(30) Foreign Application Priority Data

Dec. 15, 2014 (RU) ............................... 2014150762
Dec. 8, 2015 (KR) ........................ 10-2015-0173720

(51) Int. Cl.
| | | |
|---|---|---|
| *A61B 5/00* | (2006.01) | |
| *H04N 5/225* | (2006.01) | |
| *A61B 5/103* | (2006.01) | |
| *A61B 5/1455* | (2006.01) | |

(52) U.S. Cl.
CPC .......... *A61B 5/0077* (2013.01); *A61B 5/1032* (2013.01); *A61B 5/1455* (2013.01); *A61B 5/6898* (2013.01); *H04N 5/2251* (2013.01); *H04N 5/2254* (2013.01); *H04N 5/2256* (2013.01); *A61B 5/441* (2013.01); *A61B 2562/0233* (2013.01); *A61B 2562/185* (2013.01)

(58) Field of Classification Search
CPC .................................................... A61B 5/0077
USPC ............................................................ 348/77
See application file for complete search history.

(56) References Cited

U.S. PATENT DOCUMENTS

| | | |
|---|---|---|
| 6,157,454 A | 12/2000 | Wagner et al. |
| 6,208,749 B1 | 3/2001 | Gutkowicz-Krusin et al. |
| 6,324,417 B1 | 11/2001 | Cotton |
| 8,765,967 B2 | 7/2014 | Berg-Schultz |

(Continued)

FOREIGN PATENT DOCUMENTS

| | | |
|---|---|---|
| CN | 1889920 A | 1/2007 |
| CN | 101288103 A | 10/2008 |

(Continued)

OTHER PUBLICATIONS

Communication issued by the European Patent Office dated Nov. 2, 2017 in counterpart European Patent Application No. 15870266.2.

(Continued)

*Primary Examiner* — Eileen M Adams
*Assistant Examiner* — Daniel T Tekle
(74) *Attorney, Agent, or Firm* — Sughrue Mion, PLLC (57) ABSTRACT

An image capturing device and a sensing protection device are provided. The image capturing device includes a light source configured to emit lights on a skin, an image sensor configured to obtain an image of the skin from lights reflected from the skin, a sensing protection device, which is an attachable and detachable, configured to surround the light source and the image sensor and includes a connection unit configured to be attached to and detached from the image capturing device, and a controller configured to process characteristics of the skin based on the obtained image.

14 Claims, 8 Drawing Sheets

(56) References Cited

U.S. PATENT DOCUMENTS

| | | |
|---|---|---|
| 8,855,412 B2 | 10/2014 | Quan et al. |
| 2004/0092802 A1 | 5/2004 | Cane et al. |
| 2005/0030372 A1 | 2/2005 | Jung et al. |
| 2005/0212855 A1 | 9/2005 | Yokoyama et al. |
| 2007/0239142 A1 | 10/2007 | Altshuler et al. |
| 2009/0043363 A1 | 2/2009 | Cotton et al. |
| 2010/0185064 A1 | 7/2010 | Bandic et al. |
| 2010/0198026 A1 | 8/2010 | Young et al. |
| 2011/0105865 A1 | 5/2011 | Yu et al. |
| 2013/0072803 A1* | 3/2013 | Altshuler ............... A61B 5/445 600/476 |
| 2013/0273524 A1 | 10/2013 | Ehrenkranz |
| 2014/0018647 A1 | 1/2014 | Segman |
| 2014/0043519 A1 | 2/2014 | Azuma et al. |
| 2014/0132781 A1 | 5/2014 | Adams et al. |
| 2014/0300806 A1* | 10/2014 | Pollock ............... H04N 5/2254 348/373 |
| 2015/0286033 A1* | 10/2015 | Osborne ............ G02B 13/0045 348/345 |
| 2015/0355527 A1 | 12/2015 | Takahashi et al. |

FOREIGN PATENT DOCUMENTS

| | | |
|---|---|---|
| CN | 102348425 A | 2/2012 |
| DE | 3827457 A1 | 6/1989 |
| GB | 2429523 A | 2/2007 |
| JP | 2014-41115 A | 3/2014 |
| RU | 2003123826 A | 2/2005 |
| RU | 2294223 C2 | 2/2007 |
| WO | 9822023 A1 | 5/1998 |
| WO | 2004039255 A1 | 5/2004 |
| WO | 2014/094173 A1 | 6/2014 |
| WO | 2014103954 A1 | 7/2014 |
| WO | 2014/178806 A1 | 11/2014 |
| WO | 2015153913 A1 | 10/2015 |
| WO | 2016205950 A1 | 12/2016 |

OTHER PUBLICATIONS

Search Report dated Nov. 9, 2015, issued by the Federal Service on Intellectual Property of Russia in counterpart Russian Application No. 2014150762/14.

Office Action dated Mar. 31, 2016, issued by the Federal Service on Intellectual Property of Russia in counterpart Russian Application No. 2014150762/14.

Decision on Grant dated Aug. 11, 2016, issued by the Federal Service on Intellectual Property of Russia in counterpart Russian Application No. 2014150762/14.

Communications dated Mar. 23, 2016, issued by the International Searching Authority in counterpart International Application No. PCT/KR2015/013678.

Communication dated Apr. 10, 2019, from the State Intellectual Property Office of People's Republic of China in counterpart Application No. 201580066279.6.

Communication dated Jun. 13, 2019, from the European Patent Office in counterpart European Application No. 15870266.2.

\* cited by examiner

IMAGE CAPTURING DEVICE AND SENSING PROTECTION DEVICE

CROSS-REFERENCE TO RELATED APPLICATION

This application claims the benefit of Russian Patent Application No. 2014150762, filed on Dec. 15, 2014, in the Russian Patent Office and Korean Patent Application No. 10-2015-0173720, filed on Dec. 8, 2015, in the Korean Intellectual Property Office, the disclosure of which is incorporated herein in its entirety by reference.

BACKGROUND

1. Field

Method and apparatus consistent with exemplary embodiments relates to an image capturing device and a sensing protection device.

2. Description of the Related Art

An optical approach is an optimal solution to measuring a state of human skin according to a lot of researches on measuring chromophores and malformations of human skin. The optical solution is simple, in which a light source is used to emit light on a region of skin and reflected light is analyzed to measure a distribution of chromophores and a malformation of the skin.

This aforementioned optical approach relies on two techniques. First, the technique of precisely measuring light reflected from the skin and generating related color spectrums has been developed. Second, the technique of determining intrinsic optical parameters $m_a$, $m_s$, g, and n of the skin and mathematically modeling a light propagation process in a tissue has been developed. Light reflected in a backward direction contain information regarding various elements of a skin (for example, melanin, hemoglobin, water, carotene, and bilirubin). Reflectance spectroscopy is a well-known approach for distinguishing chromophores of a skin from each other and measuring a meaningful distribution of a specific chromophore in a skin according to the concentration thereof. In this approach, lights having different wavelengths are emitted on a test region of a skin. The lights are emitted on the skin and interact with the chromophores of the skin according to the qualities of the elements of the skin or scattering of the lights. The difference between the spectrums of images of a skin caused by ultraviolet radiation has been used to detect damages to the skin caused by sunlight in early stages.

Among the human senses, sight and color perception are perhaps the most interesting. With the digital revolution, color has become even more accessible. Among the optical methods of skin investigation, colorimetry is one of the most advanced.

Colorimetry has been used as an objective measure of perceived skin color by human eye to detect and score physiological responses of the skin from the various external stimulus.

Devices for measuring chromophores and malformation of a human skin are relatively huge in size, expensive due to their optics elements, and have limited data processing ability because of the restrictions of their internal processing units or necessity to use external data processing units (e.g., a PC).

SUMMARY

Provided are an image capturing device which is handy and is capable of measuring a state of a skin by maintaining a measurement environment constant, and a sensing protection device configured to be attachable to and detachable from the image capturing device.

Additional aspects will be set forth in part in the description which follows and, in part, will be apparent from the description, or may be learned by practice of the presented exemplary embodiments.

According to an aspect of an exemplary embodiment, an image capturing device includes a light source configured to emit lights on a skin; an image sensor configured to obtain an image of the skin from lights reflected from the skin; a sensing protection device, which is attachable and detachable, configured to surround the light source and the image sensor, the sensing protection device including a connection unit configured to be attached to and detached from the image capturing device; and a controller configured to process characteristics of the skin based on the obtained image.

According to an exemplary embodiment, an inside of the sensing protection device includes a light-absorbing material.

According to an exemplary embodiment, the image capturing device may further include a light sensing element and a white-light source.

According to an exemplary embodiment, the sensing protection device may have a telescopic function.

According to an exemplary embodiment, a height of the sensing protection device is extensible according to a focal length of a camera.

According to an exemplary embodiment, the sensing protection device may have a height determined by a focal length of the image capturing device.

According to an exemplary embodiment, the image sensor may include a color photosensitive element array having a spectral sensitivity for covering a visible region.

According to an exemplary embodiment, the connection unit of the sensing protection unit may include at least one among a magnet, a slide, and a case.

According to an aspect of an exemplary embodiment, a sensing protection device includes a sensing protection member configured to surround a light source and an image sensor included in an image capturing device; and a connection member configured to connect the sensing protection member to the image capturing device such that the sensing protection member is attachable to and detachable from the image capturing device. Light is emitted on a skin from the light source of the image capturing device via the sensing protection member, and an image of the skin generated from lights reflected from the skin is captured by the image sensor.

According to an exemplary embodiment, an inside of the sensing protection member includes a light-absorbing material.

According to an exemplary embodiment, the sensing protection member may have a telescopic function.

According to an exemplary embodiment, a height of the sensing protection member may be extensible according to a focal length of a camera.

According to an exemplary embodiment, the sensing protection member may have a height determined by a focal length of the image capturing device.

According to an exemplary embodiment, the connection member may include at least one among a magnet, a slide, and a case.

According to an aspect of an exemplary embodiment, a method of determining contents of chromophores of a skin by using a portable skin chromophores measuring device includes generating measurement conditions beforehand by using an opaque material of a sensing protection device surrounding a white-light source and an image sensor; emitting light using the white-light source of the portable skin chromophores measuring device; receiving light reflected from a skin by using an optical system of the portable skin chromophores measuring device; detecting the light and generating at least one image by using the image sensor of the portable skin chromophores measuring device; determining three-color coordinates of each of the at least one image by using a processor of the portable skin chromophores measuring device; performing mathematical modeling to simulate a radio wave of a visible spectrum range in a biological tissue by using the processor of the portable skin chromophores measuring device, based on the measurement conditions; comparing the three-color coordinates with a result of performing the mathematical modeling; and determining contents of the chromophores of the skin, based on a reflected spectrum of the skin.

According to an exemplary embodiment, the mathematical modeling may be performed using the Monte Carlo algorithm, and a skin model used in the Monte Carlo algorithm may vary according to a portion of a body.

According to an exemplary embodiment, at least one among a structure of the skin, parameters of an experiment, measurement elements, sizes and shapes of incident light and detected light may be taken into account in the Monte Carlo algorithm.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Reference will now be made in detail to exemplary embodiments, examples of which are illustrated in the accompanying drawings, wherein like reference numerals refer to like elements throughout. Also, a structure of an electronic device and a method of operating the electronic device according to an exemplary embodiment will be described in detail with reference to the accompanying drawings.

It will be understood that, although the terms "first," "second," etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the scope of the inventive concept. The term 'and/or' includes any and all combinations of one or more of the associated listed items.

The terminology used herein is for the purpose of describing particular embodiments only and is not intended to limit of the inventive concept. As used herein, the singular expression does not limit the present disclosure to have a singular component or step. Instead, the present disclosure may comprise multiple components or steps even it is described in a singular express. It will be further understood that the terms 'comprise' and/or 'comprising,' when used in this specification, specify the presence of stated features, integers, steps, operations, elements, and/or components, but do not preclude the presence or addition of one or more other features, integers, steps, operations, elements, components, and/or groups thereof.

As used herein, expressions, such as "at least one of," when preceding a list of elements, modify the entire list of elements and do not modify the individual elements of the list.

Hereinafter, exemplary embodiments will be described with reference to the accompanying drawings.

In order to direct the aspects of the exemplary embodiments described above, an image capturing device including an opaque sensing protection device providing conditions required to detect light scattered in a backward direction, a white-light source for covering a visible spectrum domain from 350 nm to 800 nm and unidirectional radiation, and a color photosensitive element array configured to detect scattered light are used. Also, it is assumed that any portion of a human body (a change in a skin type, a change in a thickness of a layer of fat, etc.) can be tested and a test region is large, e.g., 10 cm². When the sensing protection device is used, an image may be detected at any time in the same illumination state and the same detection mode. Thus, the color coordinates of an image may be associated with an actual physical wavelength in a visible region.

Because the sensing protection device may have an arbitrary shape and a telescopic function, the sensing protection device may be used in a mobile device including a flash and a camcorder. Owing to an opaque material of the sensing protection unit, the concentration of the chromophores of the skin may be measured under different kinds of external conditions (e.g., under natural light, under artificial light, when the amount of light is insufficient, etc.). A reference white color (e.g., BaSO4) of an image may be normalized to compensate for instability of a light source (a change in a battery potential, a change in a source spectrum intensity, dust, etc.). A versatile property of an exemplary embodiment applicable to various types of platforms is secured because the height of the sensing protection device may be changed (a telescopic function).

Figure 1:
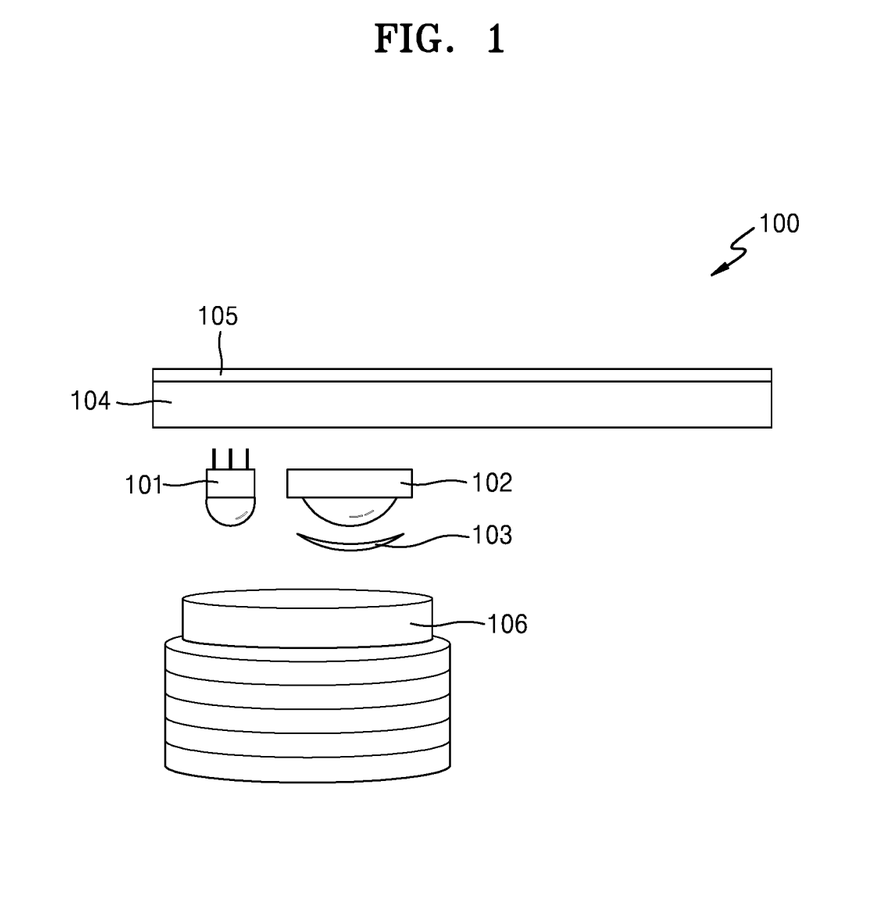
FIG. 1 is a diagram schematically illustrating an image capturing device according to an exemplary embodiment.

FIG. 1 is a diagram schematically illustrating an image capturing device 100 according to an exemplary embodiment.

Referring to FIG. 1, the image capturing device 100 includes a light source 101, an image sensor including a lens 103 and a photosensitive element array 102, a processor 104, a display 105, and a sensing protection device 106.

The light source unit 101 emits white light on a skin. The image sensor 102 detects scattered light. The processor 104 converts the detected light into an electrical signal. The electrical signal may be a digital image. The electrical signal is processed according to an image processing algorithm determined beforehand by the processor 104 and is then displayed on the display 105.

The sensing protection device 106 may provide detection conditions, e.g., an angle between a detector/light source and a region to be tested, exclusion of ambient light, etc.

The sensing protection device 106 may be opaque. The opaque property of the sensing protection device 106 may be an important factor that defines measurement conditions. When the sensing protection device 106 is opaque, ambient light may be excluded and this factor may be taken into account during a light transfer calculation.

The sensing protection device 106 has an arbitrary shape and a telescopic function. The inside of the sensing protection device 106 may be coated with a light-absorbing material. The type of a coated surface (e.g., a reflective type or absorbing type) of the sensing protection device 106 is an important parameter in light transfer calculation because the contents of chromophores of the skin depend on the type and current state of the skin. When the coated surface is the absorbing type, the color of a final skin image is changed by randomly reflected lights and thus all optical components reflected again may be excluded. When the coated surface is the reflective type, contribution of all components reflected may be taken into account, which may cause a calculation algorithm to be changed. The reflective or absorbing characteristic of the coated surface are characteristics of an anode that reflects or absorbs light. In the exemplary embodiments set forth herein, reflective or absorbing characteristics of a sensing protection device may be taken into account.

In the exemplary embodiments set forth herein, a reflection coefficient may be set to be in a visible range that does not exceed 4% to 5% when an inside of a sensing protection device is coated with an absorbing material, and may be set to be in a visible range that does not exceed 95% to 99% when an inside of a sensing protection device is coated with a reflective material.

A reference image of a standard white color (e.g., BaSO4) may be normalized in order to compensate for instability of a light source (a change in a battery potential, a change in a source spectrum intensity, a change in a state of a protection coating layer, dust, etc.). Small patterns, such as dots or other skin formations, are ignorable. Effects of a change in a battery potential, a change in a source spectrum intensity, dust, etc. may be also ignorable.

According to an exemplary embodiment, the sensing protection device 106 may have an arbitrary shape and the height thereof may be determined by an initial focal length of a camera lens of the image capturing device 100 and requirements for a field of view (i.e., a region of a skin to be tested). Homeostasis of melanin and red spots cannot be measured using the image capturing device 100 without the sensing protection device 106 because a process of measuring homeostasis of melanin and red spots may need to be performed under specific conditions, such as a specific angle of capturing, detection of an under-exposure state, etc.

According to an exemplary embodiment, a back focal length of an optical system employed in the image capturing device 100 may be decreased to decrease the height of the sensing protection device 106. The back focal length means the distance from a surface to a back focus. The height of the sensing protection device 106 may be decreased to 0.5 cm. To this end, a focal reducer may be added to the image capturing device 100. In this embodiment, the focal reducer is a positive lens in which a decrease in a focal distance may be calculated by the following equation:

$$R=1-D/FR,$$

wherein "R" denotes a decreased focal distance coefficient, "D" denotes a distance to an image plane, and "FR" denotes a focal distance of a lens. For example, when a lens having a focal distance of 100 mm is located at a distance of 20 mm from the image plane, the focal distance may decrease by 0.8 (=1−20/100). An achromatic lens may be additionally used to detect macro-images.

The image capturing device 100 may be a device including a light source and an image sensor to emit light and detect reflected light from the emitted lights and including a processor to process the detected light. Examples of the image capturing device 105 may include a mobile phone, a smart phone, a smart watch, a tablet device, a notebook device, etc.

As described above, the sensing protection device 106 capable of providing measurement conditions may be included in the image capturing device 100. The sensing protection device 106 may be a portable device to decrease a measurement error caused by an external optical condition. Also, device usability may be increased using a small-sized portable device, and a region to be measured may be easily located by dynamically configuring the device. Also, the contents of chromophores may be monitored and an image capturing angle may be maintained constant regardless of the type of external light, under any environment in which external light is not present, or regardless of the type of the skin.

Figure 2:
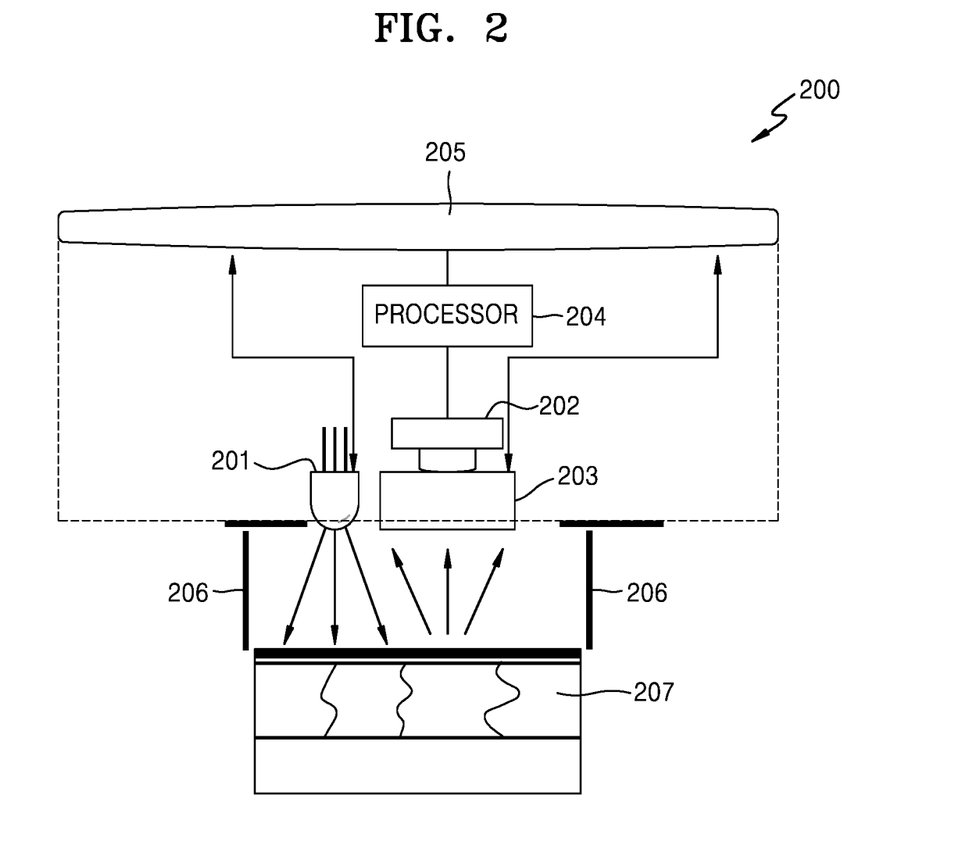
FIG. 2 is a diagram schematically illustrating an image capturing device according to an exemplary embodiment.

FIG. 2 is a diagram schematically illustrating an image capturing device 200 according to an exemplary embodiment.

Referring to FIG. 2, the image capturing device 200 includes a light source 201, a photosensitive element array 202, a camera lens 203, a processor 204, a display 205, and a sensing protection device 206.

A skin 207 is prepared. Data regarding the contents of melanin and hemoglobin in the skin 207 may be obtained by performing two operations, i.e., defining the color coordinates of an image of the skin 207 and comparing an obtained value with a result obtained by performing mathematical modeling. A color value may be the same as a specific ratio between the concentrations of the melanin and the hemoglobin.

Figure 3:
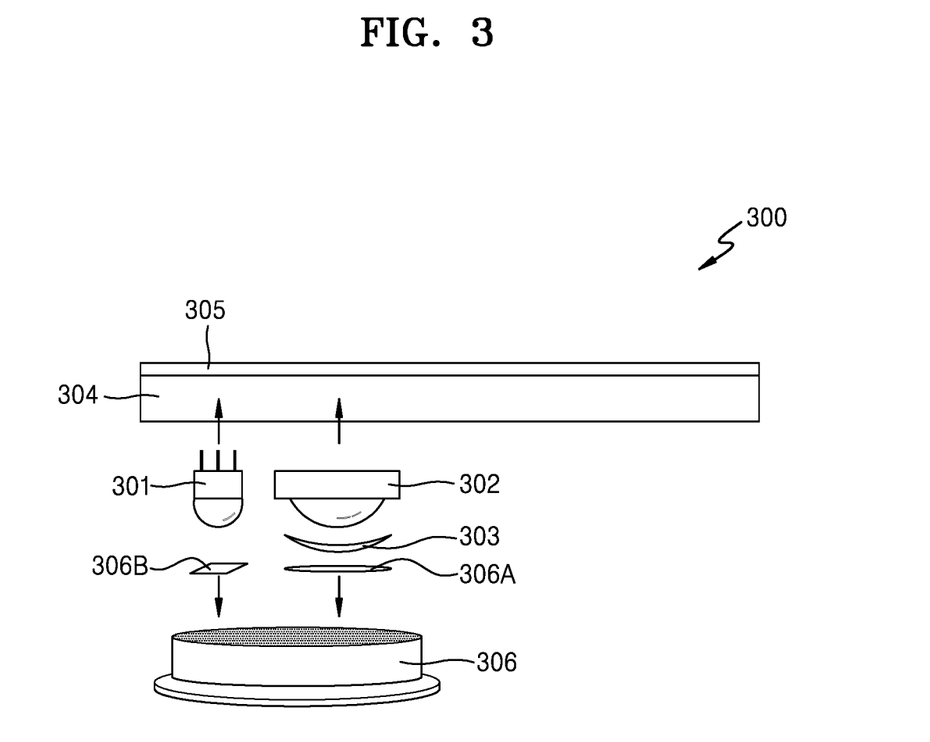
FIG. 3 is a diagram schematically illustrating an image capturing device according to an exemplary embodiment.

FIG. 3 is a diagram schematically illustrating an image capturing device 300 according to an exemplary embodiment.

Referring to FIG. 3, the image capturing device 300 includes a light source 301, an image sensor which is a photosensitive element array 302 including a lens 303 and a sensing protection device 306, a processor 304, and a display 305.

The image sensor further includes optical elements 306A and 306B and may thus decrease the height of the sensing protection device 306 by decreasing a focal length of a sensing unit. The sensing protection device 306 is embodied as an optical element. The lens 306A decreases a focal length of a camera of the image capturing device 300 and thus the sensing protection device 306 may be manufactured in a very small size. The scattering plate 306B enables regular surface radiation. The lens 306A and the scattering plate 306B may be integrally formed with the sensing protection device 306. The sensing protection device 306 may include a cover, and the inside of which has a reference white color.

As described above, the spectrum of a skin may be obtained from a user's digital photograph by using known color coordinates of an image of a region of the skin.

Figure 4:
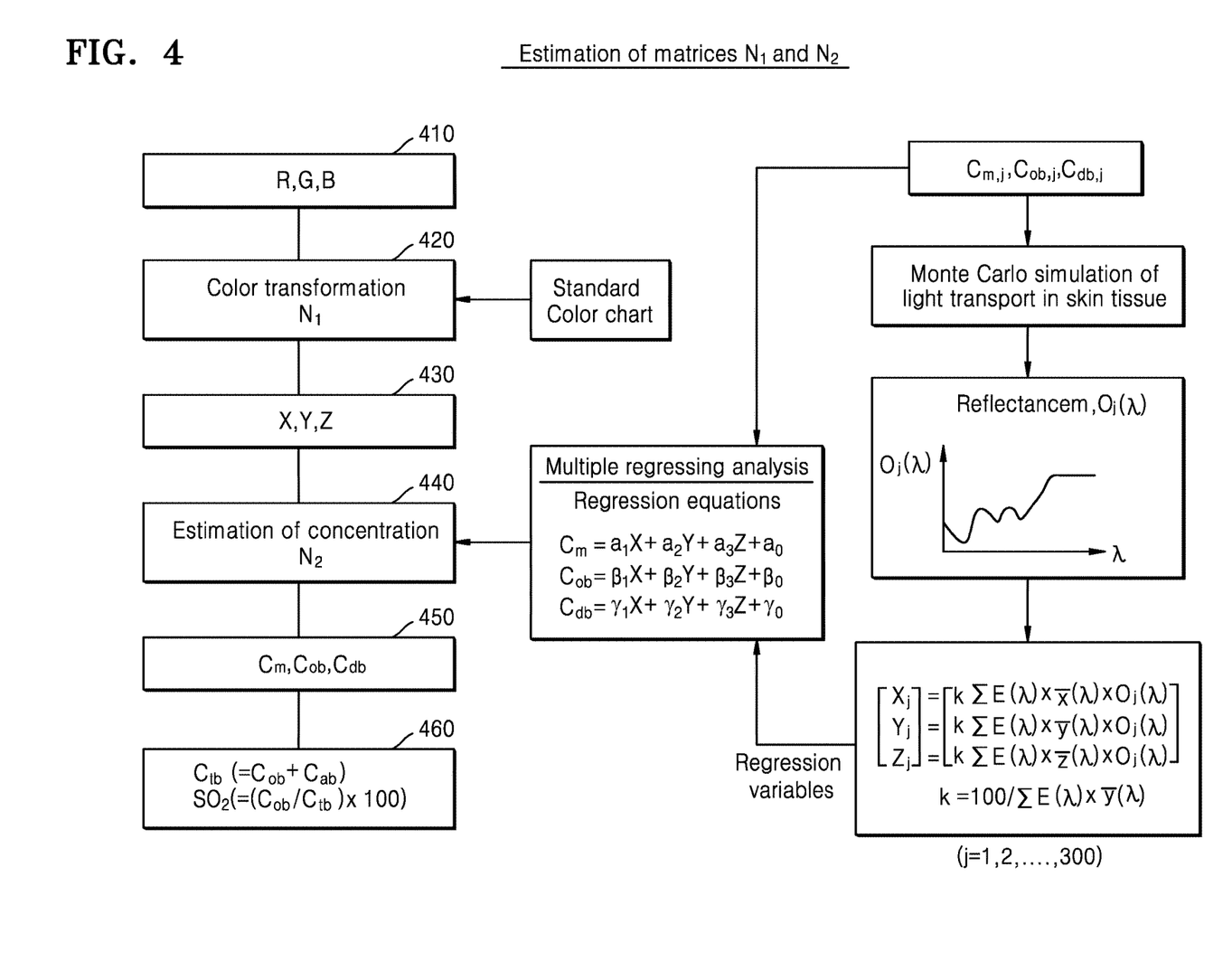
FIG. 4 illustrates an algorithm of receiving light reflected from a skin and image-processing the reflected light, according to an exemplary embodiment.

FIG. 4 illustrates an algorithm of receiving lights reflected from a skin and processing the reflected light, according to an exemplary embodiment.

Various algorithms may be used to determine the color coordinates of an image of the skin, compare obtained color values with data of the skin obtained through a simulation, and estimate the concentrations of hemoglobin and melanin in the skin.

A surface of a device on which a sensing protection device is located is placed on a region of the skin to be measured. Next, a user captures several images of a surface of the skin by using special software (SSW).

Then, using special software (SSW), the user takes a few shots of the skin surface.

The white light source radiates irradiation that is scattered by skin and focused by the optical system of a mobile device. Quantitative (brightness) and quality (color) color characteristics of the skin are determined using colorimetric systems. Three color coordinates (R, G, B) 410 are determined per pixel for each skin image using a colorimetric system for measuring skin reflectance. Then received coordinates are converted into color coordinates X, Y, Z 430 of MKO1931 (Yxy) colorimetric system and L*, a* and b* of MKO1976 (L*a*b*) colorimetric system using simple ratios. The content of hemoglobin and melanin in the human skin is estimated using an algorithm based on the inverse Monte Carlo simulation. At least two-layer model of the skin is adopted. The reflection coefficient of the skin is calculated using the Monte Carlo method in the spectral visible range. Then, the spectrum is recalculated in the color coordinate system and compared with experimentally obtained data of skin reflectance and then a match of color coordinates with its corresponding spectrum may be found. In this way, the content of melanin and hemoglobin in the skin can be estimated.

In that SSW, the RGB-values are converted into the tristimulus values in color space which is a device-independent color system and compatible with the common RGB working spaces (NTSC, sRGB, etc). Monte Carlo simulation (MCS) of light transport for human skin model is used to specify a relation among the tristimulus XYZ-values and the concentrations of melanin and blood.

Spectral composition of lights penetrating through biological tissues depends on the concentration and spatial distribution of chromophores within the given tissue, as well as on particular experimental conditions, including the probe geometry and multiple parameters of the incident optical radiation.

In this embodiment, the algorithm is a computational technique specially developed for simulation of the visible reflectance spectra of human skin and skin color calculation. The computational data are compared with the experimental data obtained using high-dynamic range measurements through different parts of a human body, which are easily accessible through those measurements. Owing to a wide range of actual probing conditions and a very complex composite structure of tissues, no general analytical solution is available for simulating the detected scattered optical radiation and its interaction with tissues, their structural malformations and/or physiological changes. Therefore, stochastic Monte Carlo (MC) modeling was employed. In this embodiment, an object oriented MC model is utilized. The object oriented MC model may describe photons and tissue structural components as objects, which interact each other. Thus, an object photon propagates through an object medium (or medium layer) and interacts with its constituents, such as cells, blood vessels, collagen fibers, etc. Such representation of the medium by objects makes it possible to develop realistic tissue models presenting 3D spatial variations of a biological structure. To simulate transmission spectra, a multilayered tissue model is applied. The model known from a prior art was extended to 17 layers by including muscles and bone structures.

The MC simulations were performed taking into account at least the actual probe geometry used in the experiment (see FIG. 6) utilizing $10^{10}$ of the detected photon packets. The conversion of the spectral distribution to the CIE XYZ (CIE 1976 L*a*b*) coordinates, as well as to the RGB color values, was performed using the standard CIE 2° observer and tristimulus values utilizing Galaxy Note 4 WLED illuminant. Observing the effect of the changes of tissues color due to, for example, changes of blood and/or melanin content, and variations in blood oxygenation, is of a potential use for the practical diagnostic purpose and bioengineering applications. These changes can be quantified and characterized with the developed MC model.

The main provisions of the proposed method are as follows: skin imaging in constant conditions of light detecting is provided by using specially developed lens hood; the numerical experiment of light transport in skin is performed for known conditions of light detecting and light source and results are the number of spectrums and corresponding color coordinates for different content of chromophores in skin; the captured color coordinates are compared with color coordinates and corresponded spectrums obtained with the numerical modeling.

The comparing data (numerically obtained) already contain the information about concentration of melanin and blood for particular skin image. So when a conformity is found after coordinates comparison, it is possible to find the chromophores concentration.

Relations between RGB-values and skin chromophore concentrations are as follows.

RGB values of a pixel on a skin surface image acquired by a digital camera can be expressed as:

$$\begin{pmatrix} R \\ G \\ B \end{pmatrix}^T = L_1 \times \begin{pmatrix} X \\ Y \\ Z \end{pmatrix}^T$$

Where
$X = \int_{400}^{700} E(\lambda) \bar{x}(\lambda) O(\lambda) d(\lambda)$
$Y = \int_{400}^{700} E(\lambda) \bar{y}(\lambda) O(\lambda) d(\lambda)$
$Z = \int_{400}^{700} E(\lambda) \bar{z}(\lambda) O(\lambda) d(\lambda)$ $$\begin{pmatrix} X \\ Y \\ Z \end{pmatrix}$$

are tristimulus values in CIEXYZ color system and $(\ldots)^T$ represents transposition of a vector. $L_1$ is a transformation matrix to convert XYZ values to the corresponding RGB values and it is available for each working space (NTSC, PAL/SECAM, sRGB, etc). $\lambda$, $E(\lambda)$, and $O(\lambda)$ are wavelength, spectral distribution of illuminant (absolute Galaxy diode spectrum, photometric), and the diffuse reflectance spectrum of human skin, respectively. $x(\lambda)$, $y(\lambda)$, and $z(\lambda)$ are color matching functions in the CIEXYZ color system. Integrals are executed over the visible wavelength range (400 to 700 nm). Assuming that the skin tissue mainly consists of epidermis containing the melanin and dermis containing blood, the diffuse reflectance of skin tissue O can be expressed as:

$$O = \frac{I}{I_0} = \left[ \int_0^\infty P_e(\mu_{s,e}, g_e, l_e) \exp(-\mu_{a,m} l_e) dl_e \right] \times \left[ \int_0^\infty P_d(\mu_{s,d}, g_d, l_d) \exp(-\mu_{a,b} l_d) dl_d \right]$$

where, $I_0$ and I are standard reflected light and detected light intensities, respectively. $P(\mu s, g, l)$ is the path length probability function that depends on the scattering properties as well as on the geometry of the measurements. $\mu s$, $\mu a$, $g$, and $l$ are the scattering coefficient, absorption coefficient, anisotropy factor, and photon path length, respectively. Subscripts, m, b, e, and d indicate melanin, blood, epidermis, and dermis, respectively. The absorption coefficient of each chromophore is expressed by the product of its concentration C and extinction coefficient e, thus, $\mu_a = C_e$. Therefore, the RGB values are expressed as the functions of $C_m$, and $C_b$.

In estimating skin chromophores concentrations based on RGB image, the following procedure is used. At first, the RGB values in each pixel of the skin image are transformed into XYZ values by a matrix N1 as:

$$\begin{pmatrix} R \\ G \\ B \end{pmatrix} = N_1 \times \begin{pmatrix} X \\ Y \\ Z \end{pmatrix}$$

(in each pixel of the image)

Then, the matrix $N_1$ should be determined based on measurements of Color Checker standard that has 24 color chips and it is supplied with data giving the CIEXYZ values for each chip under the specific illumination and corresponding reflectance spectra. The values of X, Y, and Z are then transformed into Cm, Cb by a matrix $N_2$. Then, diffuse reflectance spectra $O(\lambda)$ in a wavelength range from 400 to 700 nm at intervals of 5 nm by the MCS for light transport in skin tissue under various values of Cm, Cb is calculated. Then, the corresponding X, Y, and Z are obtained. In this MCS, the absorption coefficient of melanin for Cm is input to the epidermis as $\mu_a$, m. The absorption coefficient of blood for Cb is input to dermis as $\mu_a$ and db. The layer thickness of epidermis and dermis are set as 0.05 mm and 5.05 mm, respectively. Refractive index for each layer is assumed to be 1.4. The XYZ-values are then calculated based on the simulated $O(\lambda)$. The above calculations are executed for various combinations of Cm, Cob, and Cdb to obtain the data sets of chromophore concentrations and XYZ-values. The multiple regression analysis with data sets established the two regression equations for Cm, and Cb as:

$Cm = a_0 + a_1 X + a_2 Y + a_3 Z$, $Cb = b_0 + b_1 X + b_2 Y + b_3 Z$,

The regression coefficients ai, bi (i=0, 1, 2, 3) reflect the contributions of XYZ-values to Cm, and Cb, respectively, and are used as the elements of a 4-by-3 matrix $N_2$. Transformation with $N_2$ from the tristimulus values to the chromophore concentrations is thus expressed as:

$$\begin{pmatrix} C_m \\ C_b \end{pmatrix} = N_2 \times \begin{pmatrix} X \\ Y \\ Z \\ 1 \end{pmatrix}$$

Once the matrices $N_1$ and $N_2$ are determined, images of $C_m$, and $C_b$ are reconstructed without the MCS. The proposed technique differs from existing solutions by adding unique experiment conditions and by adding unique total spectrum of Galaxy diode.

An image capturing device may display information regarding the contents of the chromophores of a region of the skin to be tested within several seconds after lights are emitted on the skin by using a sensing protection device and an image processing algorithm as described above.

According to an exemplary embodiment, the image capturing device may further display color information of the region of the skin, a warning about a possibility that a user will suffer from sunburn, a tip for protecting the user's skin, etc.

A method of providing a user with information and the types of information to be provided to the user may be variously determined. A color density may be presented using a value or a two-dimensional (2D) color distribution map.

According to an exemplary embodiment, information regarding a state of the skin may be transmitted to a doctor or a cosmetician. For example, information regarding a medical institution may be registered with an image capturing device, and the image capturing device may automatically transmit information regarding a state of the skin to the registered medical institute whenever the image capturing device measures the state of the skin and obtains measurement data.

Various methods may be used to attach a sensing protection device to the image capturing device.

The image capturing device and the sensing protection device include various connection units.

According to an exemplary embodiment, a connection unit connecting the image capturing device and the sensing protection device may include a magnet.

Figure 5:
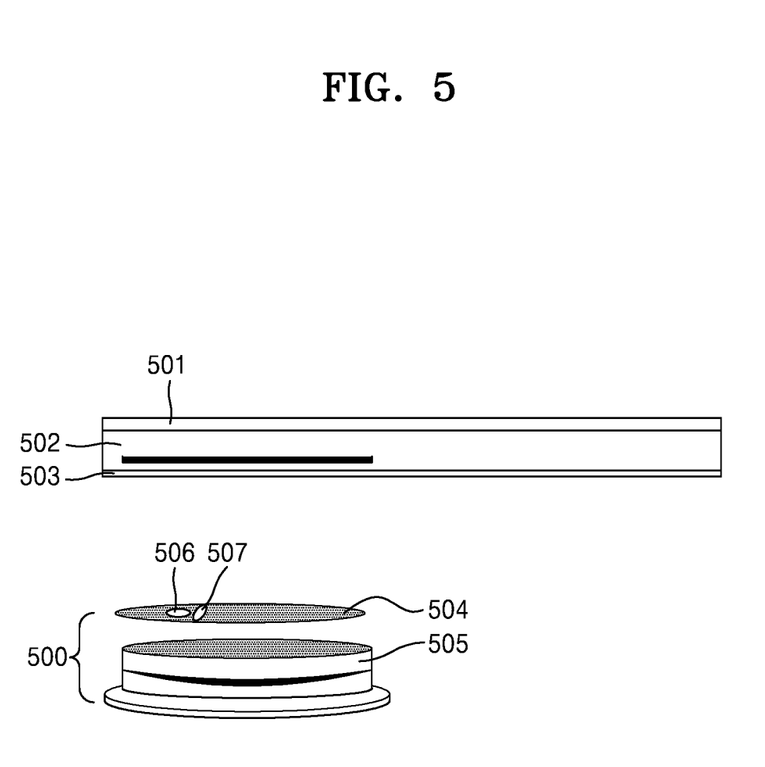
FIG. 5 is a diagram illustrating a sensing protection device using a magnet as a connection unit according to an exemplary embodiment.

FIG. 5 is a diagram illustrating a sensing protection device 500 using a magnet as a connection unit according to an exemplary embodiment.

Referring to FIG. 5, a metal plate 502 is located behind a rear-surface cover 503 of an image capturing device 501. In this case, the sensing protection device 500 may include the metal plate 502 and a magnet unit 504 as parts of the sensing protection device 500. The sensing protection device 500 may be attached to the image capturing device 501 via the magnet unit 504.

The magnet unit 504 may include a hole 506 through which a light source passes, and a hole 507 through which light reflected from the skin passes.

According to an exemplary embodiment, a connection unit connecting an image capturing device and the sensing protection device 500 may include a slide.

Figure 6:
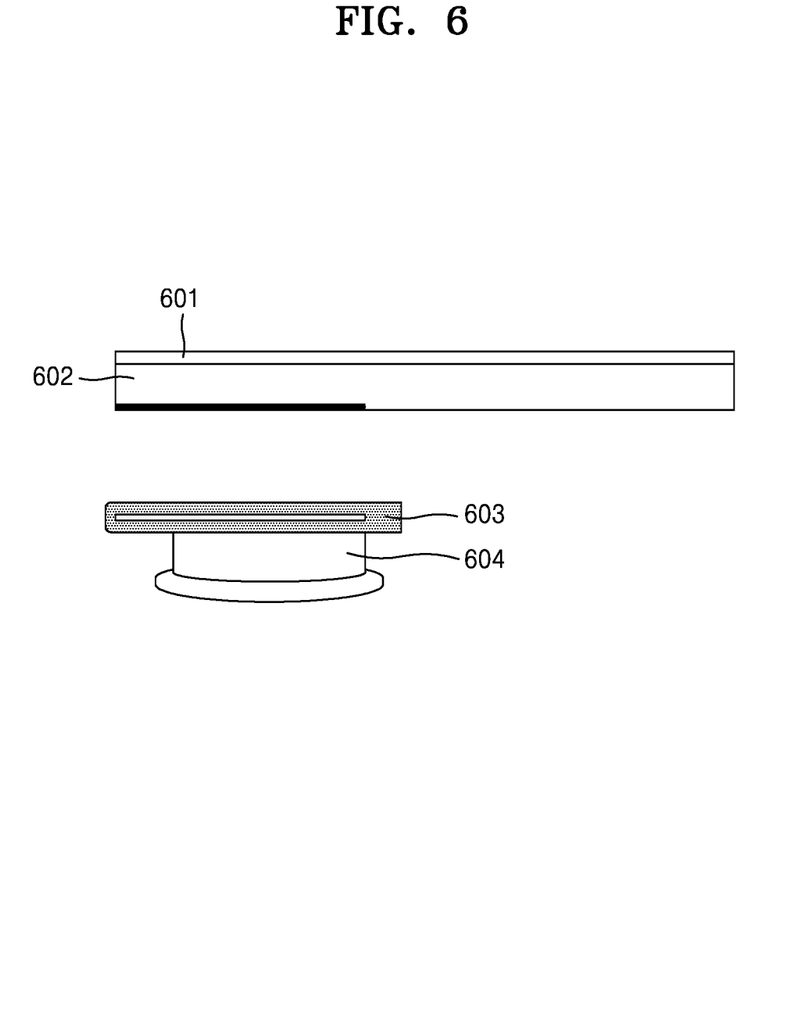
FIG. 6 is a diagram illustrating a sensing protection device using a slide as a connection unit according to an exemplary embodiment.

FIG. 6 is a diagram illustrating a sensing protection device 604 using a slide as a connection unit according to an exemplary embodiment.

Referring to FIG. 6, the sensing protection device 604 includes, as connection units, a slide groove 602 and a slide 603 to fix the sensing protection device 604 onto an image capturing device 601.

The sensing protection device 604 and the image capturing device 601 may be connected by inserting the slide 603 included in the sensing protection device 604 into the side groove 602 formed in a rear surface of the image capturing device 601 such that the slide 603 is moved into the slide groove 602 in a sliding manner.

According to an exemplary embodiment, a connection unit connecting the image capturing device 601 and the sensing protection device 604 may include a case.

Figure 7:
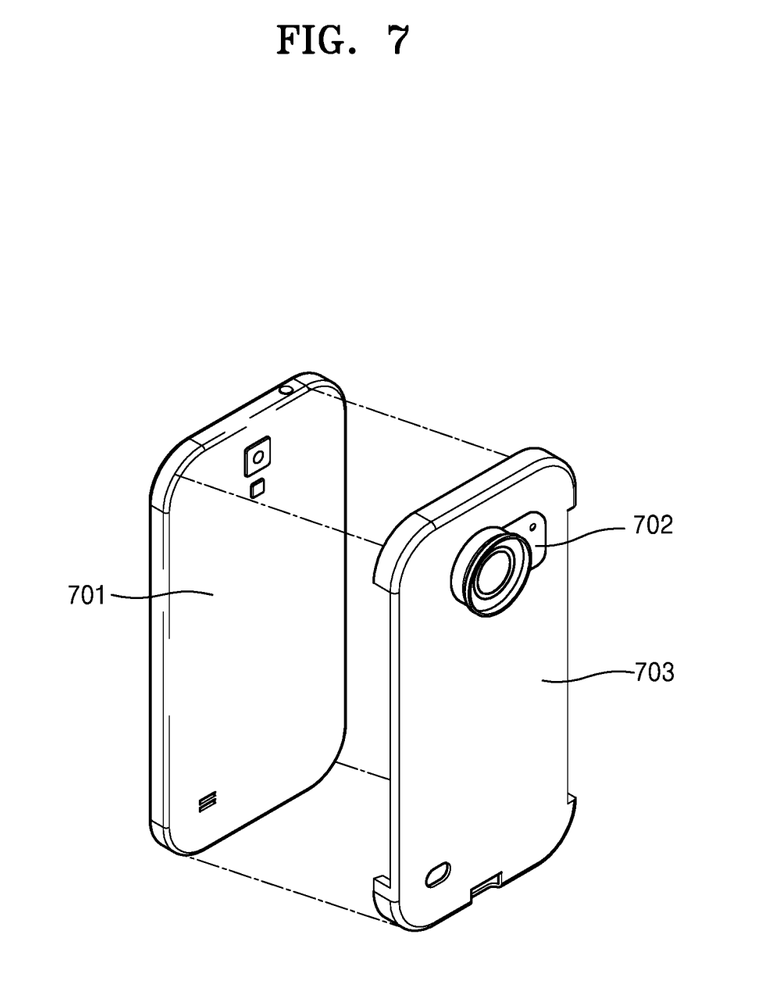
FIG. 7 is a diagram illustrating a sensing protection device using a case as a connection unit according to an exemplary embodiment.

FIG. 7 is a diagram illustrating a sensing protection device 702 using a case as a connection unit according to an exemplary embodiment.

Referring to FIG. 7, the sensing protection device 702 may be included in a phone case 703. In this case, the sensing protection device 702 may be a part of the plastic case 703. The image capturing device may be fixed on the case 701. Therefore, the image capturing device and the sensing protection device may be connected by fixing the case 701 with the case 703.

According to an exemplary embodiment, a connection unit connecting an image capturing device and a sensing protection device may include a leg.

Figure 8:
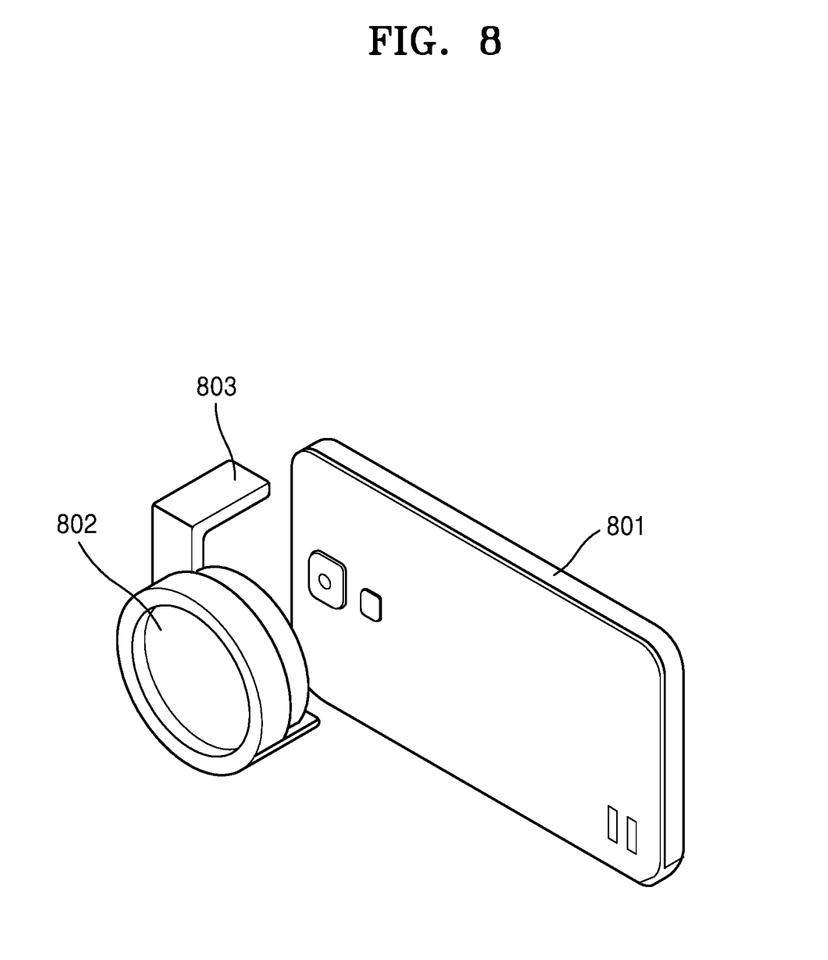
FIG. 8 is a diagram illustrating a sensing protection device using a leg as a connection unit according to an exemplary embodiment.

FIG. 8 is a diagram illustrating a sensing protection device 802 using a leg as a connection unit according to an exemplary embodiment.

Referring to FIG. 8, the sensing protection device 802 may include a leg 803 for attaching the sensing protection device 802 to an image capturing device 801.

The image capturing devices according to the exemplary embodiments described above may be used as devices for predicting the contents of melanin and blood of a user's skin. The user may estimate a tanning time and predict a tanning level in the near future, based on information regarding the contents of the melanin and blood. Also, the image capturing devices may be used to estimate absolute color values of any opaque solid-type material.

The above exemplary embodiments are applicable to measuring the optical characteristics of a skin to perform a self-tanning treatment by appropriately radiating light on the skin.

The above exemplary embodiments are related to the field of medicine or skin science. A diagnosis of a state of a skin may be used to obtain objective information regarding a spatial distribution and contents of melanin, hemoglobin, and other bio-molecules in a tissue.

A quantitative estimation of optical parameters of a human skin may provide important information to a dermatologist, and may be used in the field of skin disease diagnostics or chemistry or used to investigate influences caused by environmental factors such as UV radiation, temperature, etc.

According to the exemplary embodiments set forth herein, a state of a skin may be conveniently measured using a mobile device.

According to the exemplary embodiments set forth herein, a state of the skin may be reliably measured by maintaining a measurement environment constant.

The methods of operating an electronic device described herein may be written as program commands executable via any computer means and recorded in a computer-readable recording medium. The computer-readable recording medium may include a program command, a data file, and a data structure solely or in combination. Program commands recorded in the computer-readable recording medium may be specifically designed and configured for the inventive concept, or may be well known to and usable by one of ordinary skill in the art of computer software. Examples of the computer-readable recording medium include magnetic media (e.g., hard disks, floppy disks, and magnetic tapes), optical media (e.g., CD-ROMs and DVDs), magneto-optical media (e.g., floptical disks), and hardware devices specifically configured to store and execute program commands (e.g., ROMs, RAMs, and flash memories). Examples of program commands include not only machine language codes prepared by a compiler, but also high-level language codes executable by a computer by using an interpreter.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An image capturing device comprising;
a light source configured to emit light on a skin;
an image sensor comprising a camera configured to obtain an image of the skin from lights reflected from the skin;
a sensing protection device configured to surround the light source and the camera, the sensing protection device including a connection unit configured to be attached to and detached from the image capturing device; and
a controller configured to process characteristics of the skin based on the obtained image,
wherein an inside of the sensing protection device comprises a light-absorbing material,
wherein a height of the sensing protection device is extensible according to a focal length of the camera included in the image sensor,
wherein the image capturing device further comprises a scattering plate disposed in front of the light source and a lens disposed in front of the camera and configured to decrease the focal length of the camera, and
wherein the scattering plate and the lens are disposed within the sensing protection device and surrounded by the sensing protection device.

2. The image capturing device of claim 1, further comprising a light sensing element and a white-light source.

3. The image capturing device of claim 1, wherein the sensing protection device is further configured to provide a telescopic function.

4. The image capturing device of claim 1, wherein the sensing protection device has a height determined by a focal length of the image capturing device.

5. The image capturing device of claim 1, wherein the image sensor comprises a color photosensitive element array having a spectral sensitivity for covering a visible region.

6. The image capturing device of claim 1, wherein the connection unit of the sensing protection device comprises at least one among a magnet, a slide, and a case.

7. A sensing protection device comprising:
a sensing protection member configured to surround a light source and an image sensor comprising a camera included in an image capturing device; and a connection member configured to connect the sensing protection member to the image capturing device such that the sensing protection member is attachable to and detachable from the image capturing device, wherein light is emitted on a skin from the light source of the image capturing device via the sensing protection member, and an image of the skin generated from light reflected from the skin is captured by the camera included in the image sensor, wherein an inside of the sensing protection device comprises a light-absorbing material, wherein a height of the sensing protection member is extensible according to a focal length of the camera included in the image sensor, wherein a scattering plate is disposed in front of the light source and a lens configured to decrease the focal length of the camera is disposed in front of the camera, and wherein the scattering plate and the lens are disposed within the sensing protection member and surrounded by the sensing protection member.

8. The sensing protection device of claim 7, wherein the sensing protection member is further configured to provide a telescopic function.

9. The sensing protection device of claim 7, wherein sensing protection member has a height determined by a focal length of the image capturing device.

10. The sensing protection device of claim 7, wherein the connection member comprises at least one among a magnet, a slide, and a case.

11. An image capturing device comprising;
a light source configured to emit light on a skin;
an image sensor comprising a camera configured to obtain an image of the skin from light reflected from the skin;
a removable sensing protection device configured to surround the light source and the camera included in the image sensor, the removable sensing protection device comprising a first connecting unit and a second connecting unit, the first connecting unit being located on the image capturing device, the second connecting unit being located on the removable sensing protection device, the first connecting unit and the second connecting unit being configured to be connected/disconnected with each other such that the removable sensing protection device is capable of being attached to/detached from the image capturing device; and
a controller configured to process characteristics of the skin based on the obtained image, wherein an inside of the sensing protection device comprises a light-absorbing material, wherein the image capturing device further comprises a scattering plate disposed in front of the light source and a lens disposed in front of the camera and configured to decrease the focal length of the camera, and wherein the scattering plate and the lens are disposed within the sensing protection device and surrounded by the sensing protection device.

12. The image capturing device of claim 11, wherein the first connecting unit is a metal plate and the second connecting unit is a magnet.

13. The image capturing device of claim 11, wherein the first connecting unit is a slide groove and the second connecting unit is a slide.

14. The image capturing device of claim 11, wherein the first connecting unit is a first case, the second connecting unit is a second case, and the first case and the second case are capable of being fixed with each other.

* * * * *